United States Patent [19]

Sivula et al.

[11] Patent Number: 5,052,388

[45] Date of Patent: Oct. 1, 1991

[54] METHOD AND APPARATUS FOR IMPLEMENTING ACTIVITY SENSING IN A PULSE GENERATOR

[75] Inventors: Joel E. Sivula, White Bear Lake; Robert A. Betzold, Fridley, both of Minn.

[73] Assignee: Medtronic, Inc., Minneapolis, Minn.

[21] Appl. No.: 455,717

[22] Filed: Dec. 22, 1989

[51] Int. Cl.⁵ .............................................. A61N 1/365
[52] U.S. Cl. ................................................ 128/419 PG
[58] Field of Search .................................. 128/419 PG

[56] References Cited

U.S. PATENT DOCUMENTS

| | | | |
|---|---|---|---|
| 4,250,883 | 2/1981 | Thompson | 128/419 PG |
| 4,257,423 | 3/1981 | McDonald et al. | 128/419 PG |
| 4,305,397 | 12/1981 | Weisbrod et al. | 128/419 PT |
| 4,323,074 | 4/1982 | Nelms | 128/419 PG |
| 4,379,459 | 4/1983 | Stein | 128/419 PG |
| 4,467,807 | 8/1984 | Bornzin | 128/419 PG |
| 4,476,868 | 10/1984 | Thompson | 128/419 PG |
| 4,485,813 | 12/1984 | Anderson et al. | 128/675 |
| 4,535,774 | 8/1985 | Olson | 128/419 PG |
| 4,550,370 | 10/1985 | Baker | 364/413 |
| 4,556,063 | 12/1985 | Thompson et al. | 128/419 PT |
| 4,730,619 | 3/1988 | Koning et al. | 128/419 PG |
| 4,750,495 | 6/1988 | Moore et al. | 128/419 PG |
| 4,771,780 | 9/1988 | Sholder | 128/419 PG |
| 4,803,987 | 2/1989 | Calfee et al. | 128/419 PG |
| 4,807,629 | 2/1989 | Baudino et al. | 128/419 PG |
| 4,856,523 | 8/1989 | Sholder et al. | 128/419 PG |
| 4,867,162 | 9/1989 | Schaldach | 128/419 PG |
| 4,870,968 | 10/1989 | Wiertzfeld et al. | 128/419 PG |
| 4,890,617 | 1/1990 | Markowitz et al. | 128/419 PG |

OTHER PUBLICATIONS

Technical Manual for the Synchrony Model 2020T Pacemaker, Mar. 8, 1988–9190643-001 Rev. A.
Legend Technical Manual–8416/8417/8418–Mar. 1989.
Medtronic, Inc. Investigator Agreements.

*Primary Examiner*—William E. Kamm
*Assistant Examiner*—Scott M. Getzow

[57] ABSTRACT

A cardiac pacemaker system of the type including a sensor responsive to the metabolic demand for oxygen and which varies the pacing rate in response to the output of the sensor. The pacemaker defines a function relating sensor output to pacing rate, based upon independently selectable parameters, including a first rate which may be the lower rate of the pacemaker, a second rate which may also be the upper rate of the pacemaker, and a predetermined activity level. The function defined by the pacemaker varies the pacing rate between the first and second rates, with the second rate being achieved at the selected sensor output. The pacemaker system provides both simplicity and extraordinary flexibility, allowing rate responses to be optimized to the needs of a individual patients.

14 Claims, 11 Drawing Sheets

5,052,388

METHOD AND APPARATUS FOR IMPLEMENTING ACTIVITY SENSING IN A PULSE GENERATOR

BACKGROUND OF THE INVENTION

This invention generally relates to cardiac pacemakers and more specifically relates to cardiac pacemakers of the type which measure the metabolic demand for oxygenated blood and vary the rate of the pacemaker in accordance therewith.

In recent years, pacemakers which measure the metabolic demand for oxygen and vary the pacing rate in response thereto have become widely available. Perhaps the most popularly employed method for measuring the need for oxygenated blood is to measure the physical activity of the patient by means of a piezoelectric transducer. Such a pacemaker is disclosed in U.S. Pat. No. 4,485,813 issued to Anderson et al. Alternatively, oxygen saturation may be measured directly as disclosed in U.S. Pat. No. 4,467,807 issued to Bornzin, U.S. Pat. No. 4,807,629 issued to Baudino et al and in U.S. Pat. No. 4,750,495 issued to Brumwell et al. Other parameters employed to measure the metabolic demand for oxygenated blood include right ventricular blood pressure and the change of right ventricular blood pressure over time, venous blood temperature, respiration, rate, minute ventilation, and various pre and post systolic time intervals measured by impedance or pressure sensing within the right ventricle of the heart.

In most cases, the pacemaker includes a sensor which produces an output which varies between a maximum level and a minimum level and provides for a minimum and a maximum pacing rate. In most cases, the rate varies as a linear or monotonic function of the sensor output with the pacing rate being equal to a pre-selected base rate plus an increment which is a function of the measured sensor output (pacing rate=lower rate+f (sensor output). Some temperature sensing pacemakers have employed more complex functions to take the initial dip in temperature due to the onset of exercise into account. In some cases, the function f has a selectable slope (change of pacing rate/change of sensor output) adjustable by means of an external programmer in conjunction with selectable lower and upper pacing rates. While this provides a useful and workable system, it has the disadvantage that the relation between the programned parameters and the behavior of the pacemaker is complex and often not readily apprehended.

For example, in most cases the increment to pacing rate as a function of sensor output (slope) is programmable independent of the selected upper and lower rates. Where there is a wide range of rates between the selected upper and lower rates, the selected slope f may not provide for sufficient incrementation to the base pacing rate at maximum sensor output to actually allow the pacemaker to reach the programmed upper rate. This defeats the physician's intent in selecting the programmed upper rate. Moreover, there are typically only a finite number of selectable slopes for the function relating pacing rate to sensor output so that the wider the rate between the selected upper and lower rates, the fewer available slopes will actually allow the pacemaker to vary between the selected lower and upper rates. This reduces the adjustability of the pacemaker substantially and decreases the physician's ability to fine tune the pacemaker to the patient's physical condition.

SUMMARY OF THE INVENTION

The present invention provides a method and apparatus for controlling pacing rate in a cardiac pacemaker based upon sensor output which approaches the problem of programming the pacemaker's response to the sensor in a substantially different and improved fashion. In the present invention, the physician selects an upper pacing rate and a lower pacing rate. The physician also selects one of a number of rate response settings. However, unlike the prior art pacemakers, these rate response settings do not themselves define the slope of the function relating sensor output to pacing rate. Instead, the rate response settings can be considered to define the sensor output at which the pacing rate will be equal to the programmed upper rate.

The present invention provides a function relating sensor output pacing rate which is determined by the interrelation of the physician selected lower rate, upper rate and rate response setting (sensor output at upper rate). A plurality of rate response settings are available. Thus, for each upper and lower rate, there exists a family of rate response functions specifically tailored to the selected lower and upper rates, all of which provide for excursion between the lower and upper rates within the available range of sensor outputs. Thus full adjustability is preserved regardless of upper and lower rates, and the physician's intention in programming the upper rate is never defeated by an inappropriate selection of a rate response setting.

Generally, the pacing rate is set as a function of rate response according to the following equation: RRP=MAXIMUM $(A+(B/(4(s)+D)), URP)$. In this equation, RRP equals the number of clock cycles needed to time out the pacing rate and corresponds to the escape interval of the pacemaker, s equals the output of the sensor during the preceding time interval, URP equals the upper rate interval, and A, B and D are programmable terms generated by the programmer. The values of A, B and D, hereafter referred to as the "A-term", "B-term", and "D-term", are generated in the programmer as a function of the selected upper rate (UR), lower rate (LR) and rate response (RR) settings and are programmed into storage registers in the pacemaker using conventional programming techniques. The pacemaker includes an arithmetic logic unit capable of making the necessary calculations and controlling the rate of the pacemaker based upon the calculated RRP.

Each time the physician alters the selected upper rate, lower rate or rate response setting, the programmer generates a new set of A-term, B-term and D-term values, and loads them into the program registers of the pacemaker so that the arithmatic logic unit (ALU) may calculate the RRP thereafter based upon the updated values. Regardless of which of the selected parameters has changed, the resulting function relating pacing rate to sensor output will take the same basic form, extending from the lower rate at a minimal sensor output to the upper rate at an achievable sensor output, with a sensor output required to achieve upper rate increasing as the rate response (RR) setting is increased.

DETAILED DESCRIPTION OF THE INVENTION

Figure 2A:
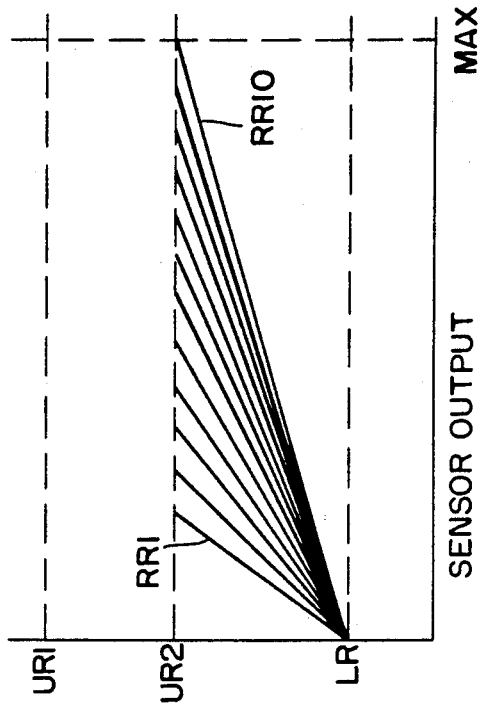
FIGS. 2A and 2B are graphs which illustrate the behavior of a pacemaker according to the present invention.
Figure 2B:
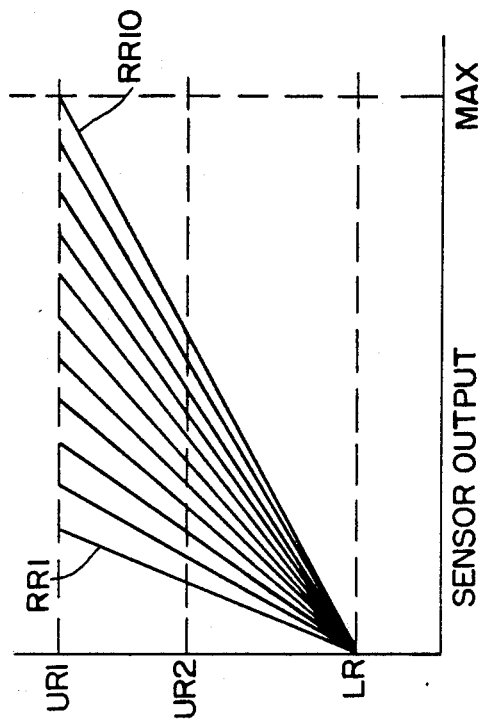
Figure 1:
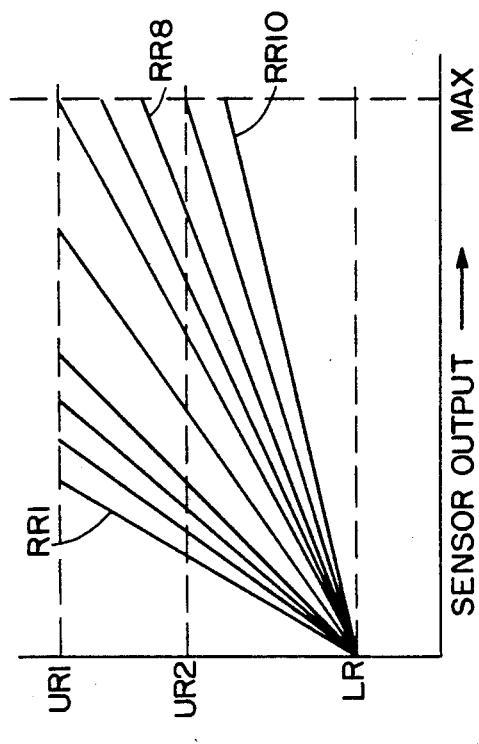
FIG. 1 is a graph illustrating the behavior of a typical prior art rate responsive pacemaker.

The distinction between the behavior of a pacemaker employing the present invention and one according to the prior art is best understood by consideration of FIGS. 1, 2A and 2B. In FIG. 1, the behavior of a typical modern rate responsive pacemaker as illustrated. In FIG. 1, the vertical axis represents pacing rate, and the horizontal axis represents sensor output from its minimum level (typically 0) to its achievable maximum output (MAX). In this drawing, the physician has selected an upper rate setting designated UR1 and a lower rate setting designated LR. Available to the physician are a number of functions interrelating pacing rate to sensor output which take the general form pacing rate=lower rate+f (sensor output). For the sake of simplicity, these are illustrated as linear functions in which the relationship of pacing rate to sensor output is programmable to display a variety of slopes (change in pacing rate per change in sensor output). However, more complex functions are also available in prior art pacers. Often, these functions display a decreasing slope as the sensor output and pacing rates increase. In some cases, this acts to aggravate the behavior discussed below. As illustrated, for some rate response selections, the pacemaker will not be capable of achieving the desired upper rate UR1. The family of curves labeled RR1-RR10 represents the available rate response settings which correspond to the slope or function selected. This system can prove problematic in several instances. For example, if the physician had initially selected the upper rate labeled UR2 and the response curve and rate response setting RR8 desiring a gradual increase from lower rate to upper rate, with upper rate being achieved only under conditions of high exercise, the pacemaker would be programmed appropriately. However, if the upper rate is increased to UR1 in an attempt to increase the patient's capacity for exercise, there would be no significant change in the behavior of the pacemaker, as UR1 cannot be achieved. Thus, simultaneous alteration of the upper rate from UR2 to UR1 and a reprogramming of the activity response RR8 to RR6 would be required. It should also be noted that at UR1, only 6 rate response settings are functionally available as compared to nine settings at UR2, as response settings 6-9 RR7-RR10 do not allow the upper rate to be achieved regardless of exercise level.

FIGS. 2A and 2B show the behavior of a pacemaker according to the present invention. Axes correspond to those in FIG. 1 with the programmed upper rate, programmed lower rate and available rate response settings illustrated. In the situation discussed above in conjunction with FIG. 1, the pacemaker of the present invention behaves quite differently. Assuming again the physician had selected UR2 as the initial upper rate and rate response setting RR8, providing a gradual increase from lower to upper rate, with upper rate being reached only in cases of strenuous exercise. A reprogramming of the upper rate in an attempt to provide the patient with greater exercise capability achieves exactly that. With the change in upper rate from UR2 to UR1, the rate response is automatically altered, with achievement of upper rate at the same level of exercise as in FIG. 2A but at the upper rate chosen by the physician in FIG. 2B. It is also important to note that even with the increase in upper rate, there are still ten available rate response settings for the physician to choose among to more closely optimize the response of the pacemaker to the patient's condition.

For functions in which the A-term is zero, the rate response curves will have a constant slope. If the A-term is positive, the slope will decrease as sensor output increases. If the A-term is negative, the slope will increase with increased sensor output.

In examining FIGS. 2A and 2B, it is important to note that the intercept of the rate response curves RR1-RR10 with the upper rate in either figure occurs at the same sensor output level. This provides for achievement of the upper rate at the same level of exercise even after changing of upper rate programming. This feature is believed to be of great benefit in simplifying the programming of the pacemaker and in assisting adjustment of the pacemaker to meet the patient's needs.

Figure 3:
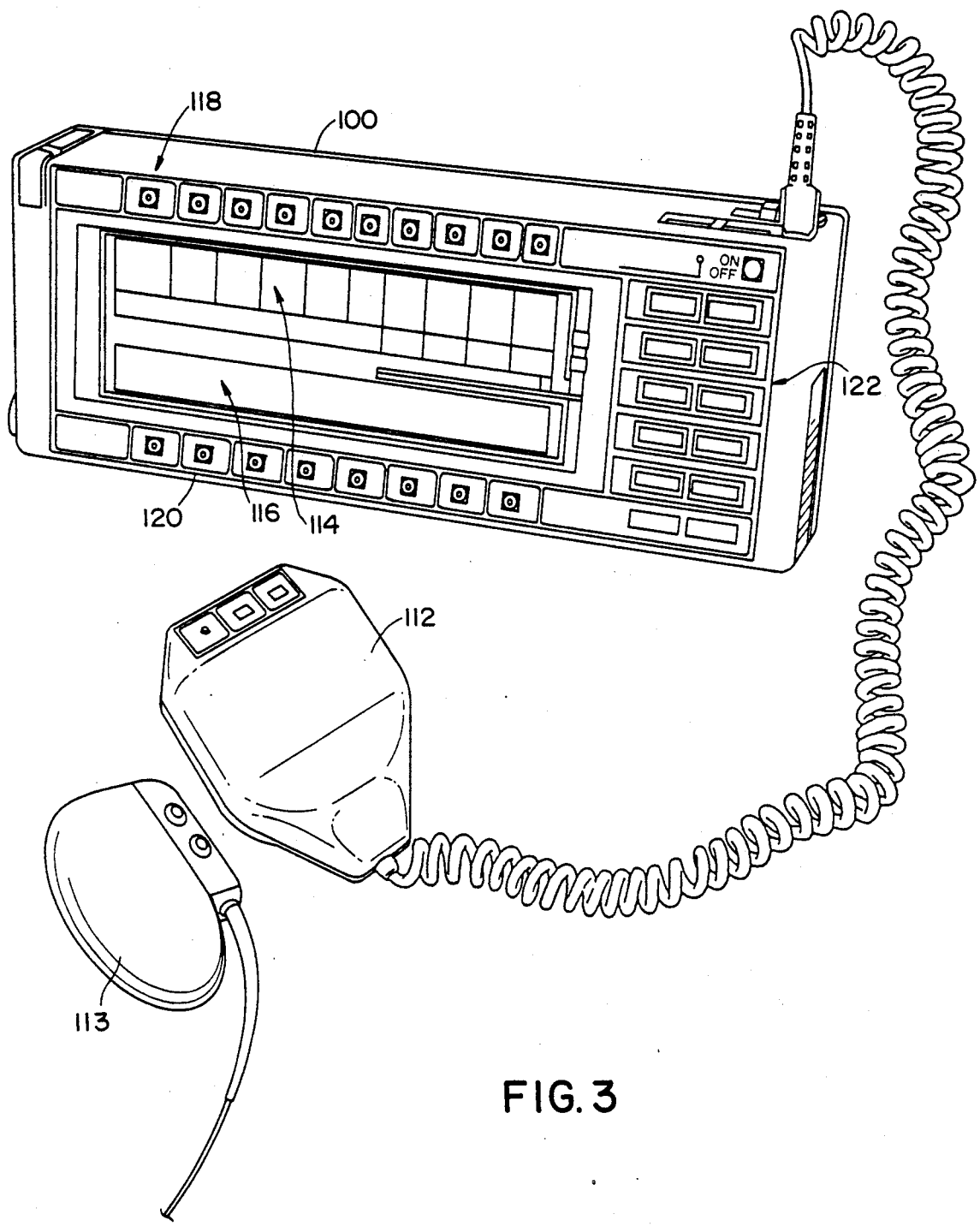
FIG. 3 shows a perspective drawing of the pacemaker and programmer as a system.

FIG. 3 shows a perspective view of the pacemaker and programmer according to the present invention. The programmer illustrated is a Medtronic Model 9710 programmer which has been commercially available for several years and is intended to be used with all Medtronic pacemakers. The programmer 100 is a microprocessor based device which provides a series of encoded signals to the pacemaker 110 by means of a programming head 112 which transmits RF encoded signals to the pacemaker 113 according to the telemetry system laid out in U.S. Pat. No. 4,305,397 issued to Weisbrod et al on Dec. 15, 1981, U.S. Pat. No. 4,323,074 issued to Nelms on Apr. 6, 1982, or in U.S. Pat. No. 4,550,370 issued to Baker on Oct. 29, 1985, all of which are incorporated herein by reference in its entirety. However, any appropriate programming methodology available to the art may be employed so long as the desired information is transmitted to the pacemaker. It is believed that one of skill in the art would be able to choose from any of a number of available programming techniques to accomplish this task.

The programmer as illustrated is provided with alpha numeric/symbolic LCD displays 114 and 116 and several banks 118, 120 and 122 of data entry keys to facilitate selection of the desired parameter to be programmed and entry of the particular setting for the desired parameter. For purposes of the present invention, the specifics of operation of the programmer are not believed to be important with the exception that whatever programmer is used in the context of the present invention must include means for selecting an upper rate (UR), a lower rate (LR) and one of a plurality of rate response (RR) settings. Typically, this will be accomplished by means of data entry keys, with operation prompted and reflected by LCD displays 114, 116.

In the specific embodiment disclosed herein, the lower rate is programmable from 40 to 90 beats per minute in increments of 10 beats per minute. The upper rate is programmable between 100 and 170 beats per minute in increments of 10 beats per minute and there are 10 rate response settings, 1-10, are available.

In addition, the programmer 100 should include means for selection of acceleration and deceleration parameters which limit the rate of change in pacing rate. Typically, these parameters are referred to in rate responsive pacemakers as the acceleration and deceleration settings or the attack and decay settings. These may be expressed as the time interval required for the pacemaker to change between the current pacing interval and 90% of the desired pacing interval, assuming that the activity level corresponding to the desired pacing rate remains constant. Appropriate values for the acceleration time would be, for example, 0.025 minutes, 0.5 minutes and 1 minute. Appropriate values for the deceleration time would be 2.5 minutes, 5 minutes and 10 minutes.

In response to entry of the upper rate, lower rate and rate response parameters, the programmer 10 generates three numerical values for the A-term, B-term and D-term. These are the values used in the previously discussed rate response equation $RRP = A + (B/(4(s) + D))$. The best mode of accomplishing the relationship between the selected upper rate, lower rate and rate response setting is believed to be a lookup table in which values for the A-term, B-term and D-term are cross-referenced to the specific desired settings. The numerical values will, of course, vary depending upon the clock rate and number of counting stages used to determine the pacing rate by the pacemaker. However, they should be selected to provide a family of rate response curves as illustrated in FIGS. 2A and 2B defining RRP as a linear or other function of such "s" that RRP corresponds to the base rate at minimum sensor output and corresonds to the upper rate at a predetermined achievable sensor output level determined by the selected rate response (RR) setting. For example, in the pacemaker described in the present application, the sensor employed is a piezoelectric sensor as described in the above cited Anderson patent which generates an output signal due to deflection of the case of the pacemaker as a result of compression waves within the body caused by physical movement of the body. Each time the amplitude of a signal from the transducer exceeds a certain threshold, it is counted and retained. In this case, "s" is the number of counts per second from the piezoelectric sensor. The settings 1-10 of the rate response parameter correspond to (s) values of 3 to 12 counts per second from the activity sensor.

Included as an appendix is a lookup chart appropriate for use in the context of the pacemaker described below. It should be kept in mind that the specific values are optimized for the particular rate counter architecture employed by the pacemaker illustrated in the present application.

With each change of the upper rate, lower rate or rate response setting, the programmer 100 refers to the lookup table to determine the appropriate values for the A-term, B-term and D-term which are always changed in concert with one another by sequential transmission of their values and the upper rate (UR) to the pacemaker where they are used to control the pacing rate.

Figure 4:
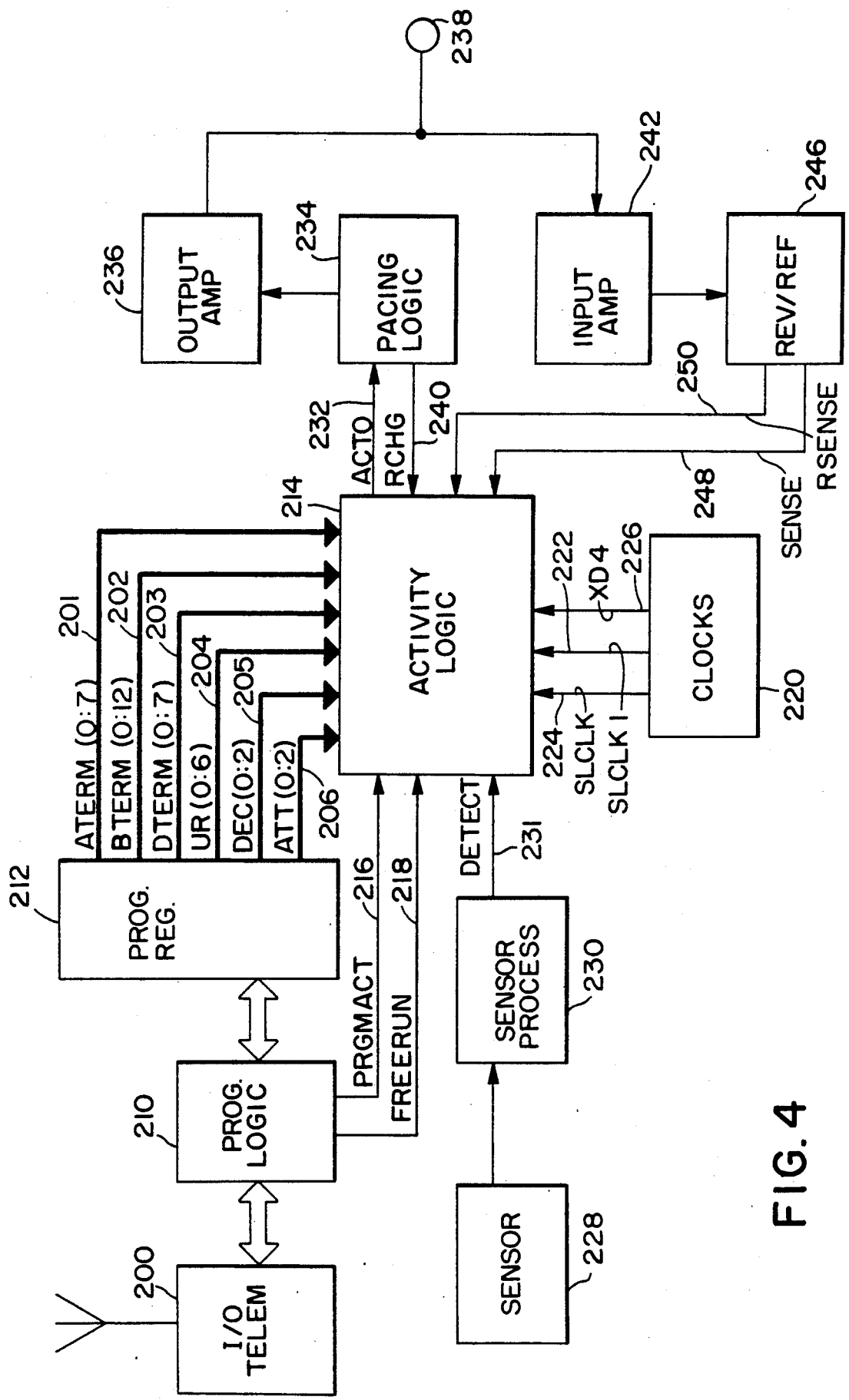
FIG. 4 is a block functional diagram showing the improved activity processing circuitry and its interconnection with circuitry of a modern activity sensing pacemaker.

FIG. 4 is a functional block diagram of the pacemaker 110 illustrated in FIG. 3. The pacemaker includes input/output telemetry 200 and programming logic 210 for receiving and storing signals from the programmer. The telemetry 200 and program logic 210 may correspond to those devices employed in U.S. Pat. No. 4,566,063 issued to Thompson et al on Dec. 3, 1985 and U.S. Pat. No. 4,257,423 issued to McDonald et al on Mar. 24, 1981, respectively, both of which are incorporated herein by reference in their entirety. However, the particular programming and telemetry scheme chosen is not critical to the present invention so long as it provides for entry and storage of the values of the A-term, B-term and D-term, the upper rate, the attack (acceleration) parameter and the decay (deceleration) parameter. As illustrated in FIG. 4, these values are stored in a bank of shift registers 212 and are provided to the activity logic 214 by means of a series of multi-bit parallel data busses 201-206. Two additional signals from the programming logic are illustrated which are beneficial in practicing the present invention. These include the PRGMACT line 216 which signals the activity logic that programming of a new set of parameters relevant to the activity logic has been completed and FREERUN line 218 which triggers a diagnostic function in which the pacemaker's rate timing circuitry runs asynchronously at the rate corresponding to RRP.

Clock signals for activity logic are provided by clock logic 220 which produces a first 126.6 Hz clock signal on 1 line 222, a corresponding second clock signal on SLCLK line 224 and a third 50% duty cycle clock signal with a 8,192 Hz frequency, divided down by 4 from a 32 KHz crystal oscillator on XD4 line 226. These clock signals provide the basic timing signals for the activity logic 214.

Also providing an input to the activity logic 214 is the sensor 228 and its associated sensor processing circuitry 230. As discussed above, the sensor takes the form of a piezoelectric crystal mounted to the interior of the can of the pacemaker, and sensor processing circuitry generates a signal each time the signal from the sensor exceeds a certain predetermined threshold. In prior art pacemakers of this general type, the threshold level for the sensor 228 has typically been programmable to vary the amount of physical exertion required in order to trigger an output from the sensor processing circuitry. As noted above, sensor 228 and sensor processing circuitry 230 may correspond to those disclosed in U.S. Pat. No. 4,428,378 issued to Anderson and Brumwell on Jan. 31, 1984. This patent is incorporated herein by reference in its entirety. Alternatively, other sensors and sensor processing circuitry could be used in conjunction with the present invention so long as the sensor processing circuitry produces an output indicative of the patient's metabolic demand for oxygenated blood.

The activity logic 214 times the basic escape interval of the pacemaker, that is the interval between successive pacing pulses in the absence of underlying natural heart activity or between a spontaneous heart beat and the next subsequent pacing pulse where natural heart activity is present. Expiration of this interval is indicated by means of a signal on ACTO line 232 which triggers pacing logic 234 to cause the output amplifier 236 to generate a pacing pulse applied to the heart via electrode 238. Electrode 238 will genrally be located in or on the ventricle of the heart, but in some cases may be located on or in the atrium. Pacing logic 234 also provides a signal on RCHG line 240 indicating the delivery of a pacing pulse by the output amplifier which is used to reset timing of the escape interval by activity logic 214.

Natural activity in the heart is sensed via electrode 238 and input amplifier 242. Input amplifier 242 generates a signal on line 244 which passes through the reversion/refractory block 246 to generate a signal on SENSE line 248 if the heart activity is sensed after expiration of the refractory period defined by refractory/reversion block 246 and to generate a signal on RSENSE line 250 if the natural activity in the heart is sensed during the refractory period defined by reversion/refractory block 246.

The pacing logic 234, output amplifier 236, input amplifier 242 and reversion/refractory period 244 may correspond to those found in any modern digital pacemaker. The output amplifier may correspond generally to the output amplifier disclosed in U.S. Pat. No. 4,476,868 issued to Thompson on Oct. 16, 1984 incorporated herein by reference in their entirety. The input amplifier 242 may correspond generally to that disclosed in U.S. Pat. No. 4,379,459, issued to Stein on Apr. 12, 1983, also incorporated herein by reference in its entirety. The pacing logic 234 and reversion/refractory blocks may correspond to those disclosed in U.S. Pat. No. 4,250,883 issued to Thompson on Feb. 17, 1981, also incorporated herein by reference in their entirety. The specific embodiments of the pacing logic 234, output amplifier 236, input amplifier 242 and reversion/refractory circuit 246 are not believed critical to the invention so long as they provide means for generating a stimulus pulse in response to timeout of the escape interval by the activity logic 214 and provide for reset of the escape interval determined by the activity logic 214 in response to either generation of a stimulus pulse or sensing of a natural contraction of the heart.

The invention of the present application as reflected in activity logic 214 is believed to be compatible with any modern sensor based pacemaker. Although the invention as described hereafter specifically focuses on an embodiment employing a piezoelectric sensor for sensing physical activity of the body, the invention is also believed employable in the context of pacemakers which sense oxygen, blood temperature, pressure or other physiologic parameters indicative of the demand for oxygenated blood.

Figure 5:
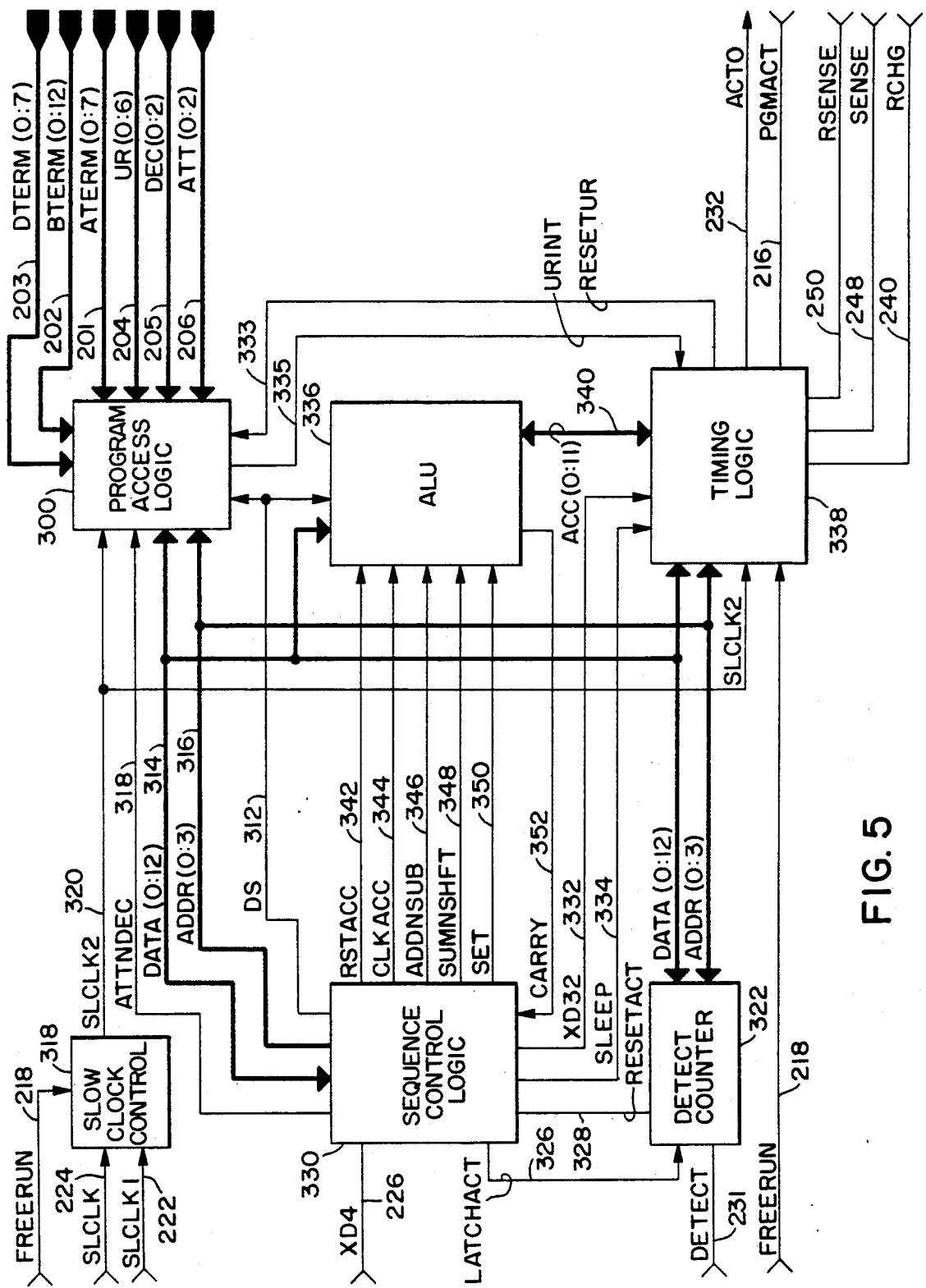
FIG. 5 is a functional schematic diagram of activity processing circuitry according to the present invention showing inputs and outputs from the circuitry and the basic functional blocks.

FIG. 5 is a functional schematic diagram of the activity logic 214 illustrated in FIG. 4. This diagram illustrates the functional interface between the major circuit blocks in the activity processing circuitry and the inputs and outputs to the remainder of the pacemaker circuitry. Data stored in the program registers 212 is provided to the program access block 300 by means of a plurality of multibit parallel data buses. These multibit buses include an 8 bit D-TERM bus 302 which carries the 8 bit value of the D-TERM, a 13 bit B-TERM bus 304 which carries the value of the B-term, an 8 bit A-TERM bus 306 which carries the value of the A-term, a 7 bit UR bus 308 which carries the value of the upper rate, a 3 bit DEC bus 310 which carries the value of the decay (deceleration) setting and a 3 bit ATT bus 312 which carries the value of the attack (acceleration) setting. Program access block 300 selectively applies the data from these various data busses to the 13 bit DATA bus 314 for use throughout the remainder of the circuitry. The selection of data for application to DATA bus 314 is made via control lines to the program access logic including a 4 bit ADDR bus 316, DS line 317, and ATTNDEC line 318. These control lines determine which of the various inputs to the program access block 300 appear on the bidirectional DATA bus 314.

One of the primary clocks employed by the circuitry is produced by the slow clock control 318 which selects between the clock signals on SLCLK 1 line 224 and SLCLK line 222. When FREERUN line 218 is high, the clock signal on SLCLK 1 line 222 is passed through to SLCLK 2 line 320. When FREERUN line 218 is low, the clock signal on SLCLK line 224 is passed through to SLCLK 2 line 320. The value of RRP is the number of cycles of the clock signal on SLCLK 2 line 320 per escape interval and corresponds to the basic pacing rate determined by the activity logic illustrated.

Inputs from the sensor 228 (FIG. 4) are applied to the activity logic illustrated by means of detect counter 322 which counts the number of signals appearing on DETECT line 231 over successive 2 second periods. Every 2 seconds, the number of signals counted by detect counter 322 is applied to DATA bus 314 under control of the 4 bit ADDR bus 324. Signals on DET(CT line 231 are counted and are stored for two successive 2 second intervals under control of LATCHACT line 326. Detect counter 322 is reset via RESETACT line 328.

Control of the basic operation of the activity logic is accomplished by the sequence control block 330. This block includes a 4 bit counter which provides the previously discussed signals on the ADDR bus 316, the ATTNDEC line 318, the LATCHACT line 326 and the RESETACT line 328, as well as numerous other control signals. The basic timing for sequence control block 330 is provided by the clock signal on XD4 line 226. This clock signal is divided by 8 to produce a 1024 Hz frequency clock on XD32 line 332. Sequence control 330 also provides a control signal on SLEEP line 334 which serves a variety of functions which will be discussed below. Sequence control circuitry 330 also controls the arithmetic logic unit (ALU) 336 which calculates the value of RRP from the 4 second counts provided by DETECT counter 322. The value of RRP is provided to the pacing timing circuitry 338 on the 12 bit ACC bus 340.

ALU 336 is a 13 bit full carry adder/accumulator controlled by sequence control block 330. Sequence control block 330 generates signals for resetting the accumulator on RSTACC line 342 for clocking the accumulator on CLKACC line 344 for selecting between addition and subtraction on ADDNSUB line 346 for selecting between summing and shifting on SUMNSHFT line 348 and for setting the first bit in the accumulator equal to 1 fia SET line 350. The carry output of the adder is provided to the sequence control 330 on CARRY line 352. The data strobe signal on DS line 312 controls the entry of information on the DATA bus 314 into the ALU 336.

Each 2 seconds the ALU 336 provides an updated value of RPP to the pacing timing 338 via the 12 bit ACC bus 340. This value determines the number of cycles of the clock signal on SLCLK 2 line 320 used to define the escape interval of the pacemaker. Timing of this escape interval is initiated by signals on RCHG line 240 or SENSE line 248 indicating the previous delivery of a pacing pulse or the sensing of natural activity in the heart outside the refractory period, respectively. At the expiration of the escape interval defined by the timing logic circuitry 338, ACTO line 342 goes high triggering generation of a stimulus pulse and the subsequent provision of a signal on RCHG line 240 to reset timing of the escape interval. A high signal on PGMACT line 216 prevents entry of a new value into the pacing timing via the accumulator bus 340 while activity response parameters A-term, B-term D-term and upper rate are being reprogrammed.

Program access logic 300 also includes an upper rate timer which determines the maximum pacing rate of the pacemaker. The upper rate timer is reset concurrently with the timing logic 338 by a signal on RESETUR line 333. Time out of the upper rate interval is indicated by a signal on URINT line 335. In the event that the escape interval corresponding to the current value of the RRP expires before the upper rate interval due to reprogramming of the upper rate to a rate lower than the current pacing period or due to the upper rate interval being reset by a signal on RSENSE line 250, the escape interval time out signal on ACTO line 232 is delayed until time out of the upper rate interval.

Figure 6:
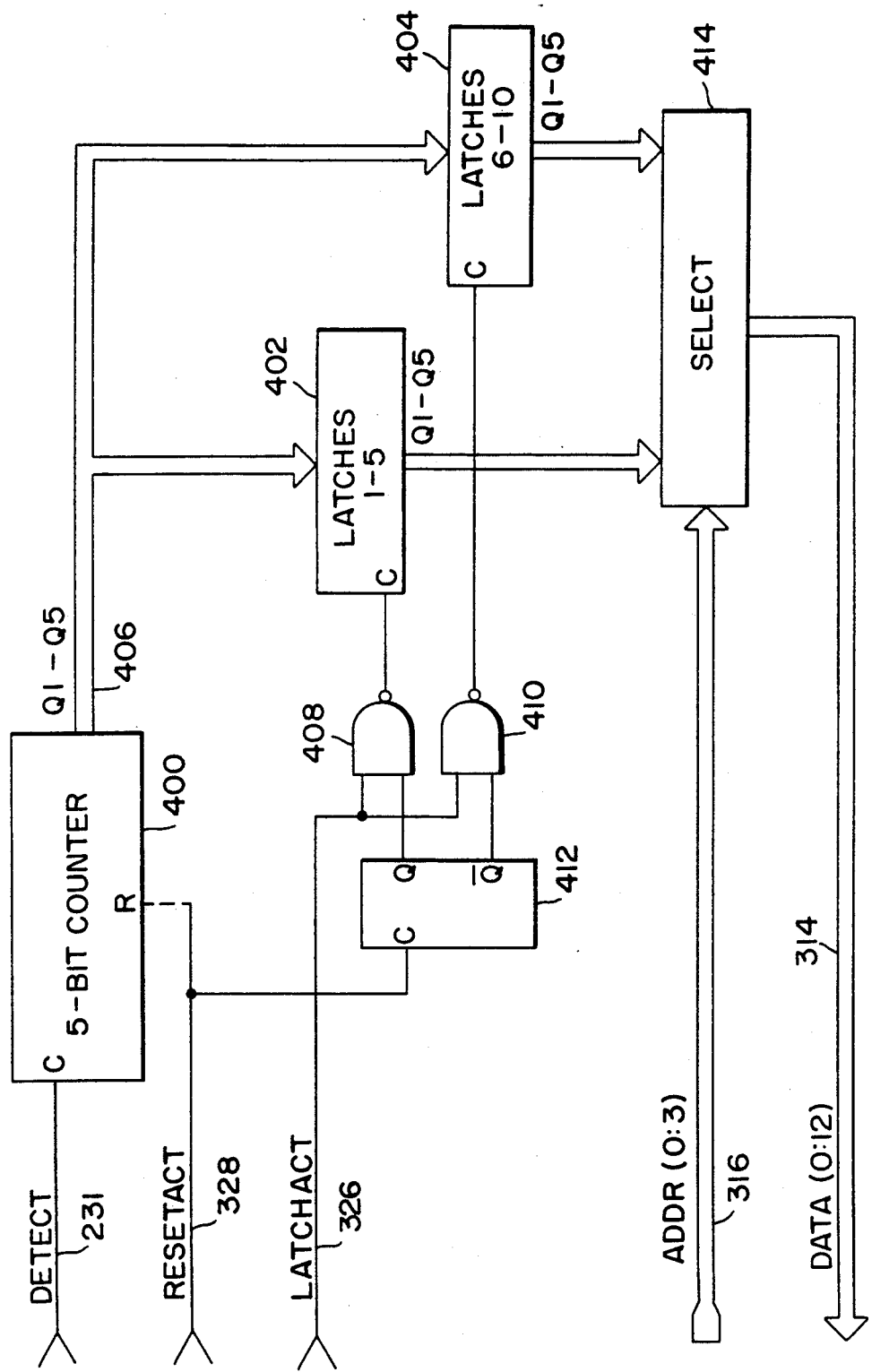
FIG. 6 is a schematic diagram of the detect counter functional block illustrated in FIG. 5.

FIG. 6 illustrates the circuitry of DETECT counter 322 in more detail.

The signals on DETECT line 231 serve to clock the 5 bit counter 400. Every 2 seconds the value of the Q outputs of the individual counting stages of counter 400 is latched into one of two sets of latches 402 and 404 via a 5 bit bus 406. Selection between latches 402 and latches 404 is accomplished by NAND gates 408 and 410 which alternately latch the values of Q1-Q5 of counter 400 into latches 402 and 404 depending upon the state of flip-flop 412 when latch ACT line 326 goes high. After the values of Q1-Q5 have been latched, sequence control circuitry 330 generates a reset pulse on line 328 which resets 5 bit counter 400 and clocks flip-flop 412 so that at the expiration of the next 2 second interval, the values of Q1-Q5 will be located into the other of the two sets of latches 402 and 404. Thus, at any time, latches 402 and 404 contain counts indicative of the number of signals on the DETECT line 231 over the previous 4 seconds. After latching the values of Q1-Q5 of counter 400, sequence control logic 330 sequentially applies the contents of latches 402 and 404 to DATA bus 314 via select logic 414. In response to a 4 bit signal 0010 on the ADDR bus 316, select logic 414 passes the contents of latches 402 through to the lines 0:4 of data bus 314. In response to a code of 0011 on ADDR bus 316, the contents of latches 6 to 10 are applied to the 5 lowest order lines 0:4 of DATA bus 314. These values are transferred to ALU 336 where they are used to calculate the value of RRP, corresponding to the pacemaker's escape interval.

Figure 7B:
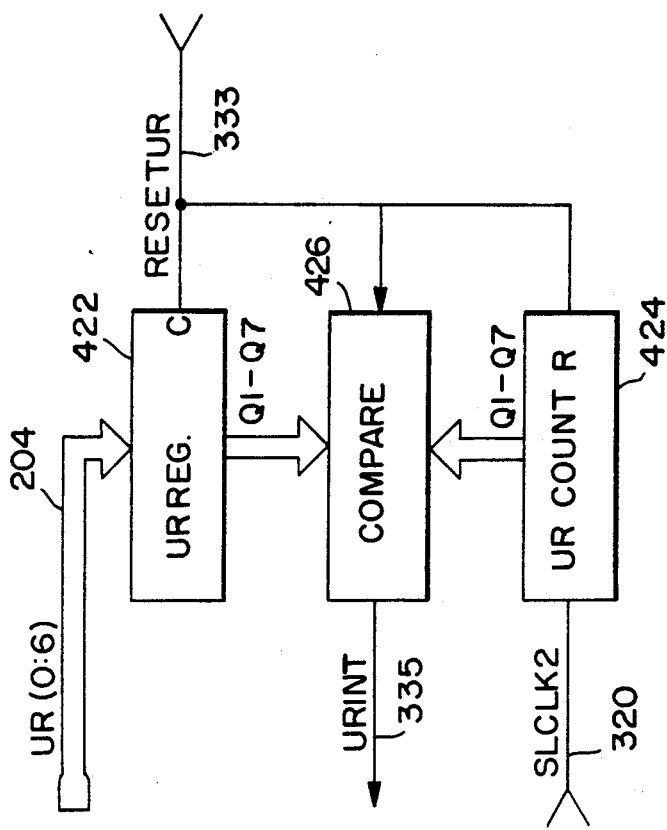
FIGS. 7A and 7B are functional diagrams of the program access block illustrated in FIG. 5.
Figure 7A:
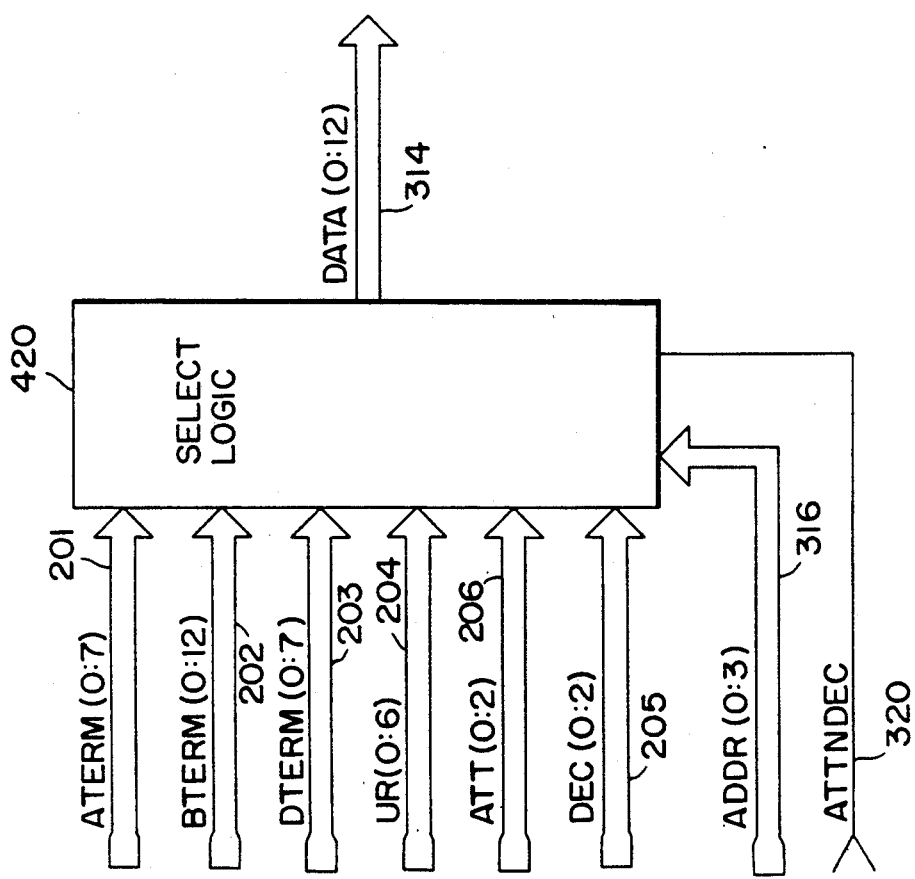

FIG. 7A illustrates in block format the data management functions of the program access block 300. Program access block 300 includes select logic 420 which applies various single and multibit signals to the DATA bus 314. Selection of which signals are applied to DATA bus 314 is controlled by the 4 bit code on ADDR bus 316 and by the state of ATTNDEC line 320. Select logic 420 operates as follows.

In response to a code of 0001 on ADDR bus 316, the values on D-TERM bus 203 are applied to lines 0-7 of DATA bus 314. In response to a code of 0100 on ADDR bus 316, select logic 420 applies the values on TERM bus 202 to lines 0-12 of the DATA bus 314. In response to a code of 0111 on ADDR bus 316, select logic 420 applies the values on A-TERM bus 201 to lines 4-12 of DATA bus 314. In response to a code of 1000 or 1001, the values on UR bus 204 indicative of the programmed upper rate are applied to lines 4-10 of DATA bus 314. In response to a code of 1011 in conjunction with a high signal on ATTNDEC line 320, the values on ATT bus 206 are applied to lines 0-2 of DATA bus 314. In response to a code of 1011 in conjunction with a low signal C line 320, the values on DEC bus 205 are placed on DATA bus 314.

In addition to providing access for the programmed parameters to the DATA bus 314, select logic 420 also provides 2 predetermined fixed values to the data bus 314 for entry into the ALU 336. In response to a code of 1111 on ADDR bus 316, select logic 420 places a 1 on line 12 of DATA bus 314 keeping all other lines low. In response to a code of 0000 on ADDR bus 316, select logic 420 places a 1 value on line 9 of DATA bus 314. In all of the above cases when select logic 420 places a value on selected lines of the DATA bus 314, all other lines are set low.

FIG. 7B illustrates the upper rate timing circuitry for the pacemaker which limits the rate at which the pacemaker will generate stimulation pulses. In response to a high signal on RESETUR line 333, the 7 bit value for the upper rate present on UR bus 308 is latched into the 7 bit upper rate register 422. Simultaneously, the 7 bit upper rate counter 424 and the comparison logic 426 are reset. Reset signals on RESETUR line 333 are generated by the pacing timing block in response to the occurrence of a signal on the RCHG line 240, sense line 248 or R sense line 250. Upper rate counter 424 is clocked by the clock signal on SLCLK 2 line 320. When the count in upper rate counter 424 corresponds to the programmed upper rate loaded in register 422, URINT line 335 from compare logic 426 is latched high indicating time out of the upper rate period. The signal on URINT line 335 is provided to the timing logic 338 and enables triggering of a pacing pulse.

Figure 8:
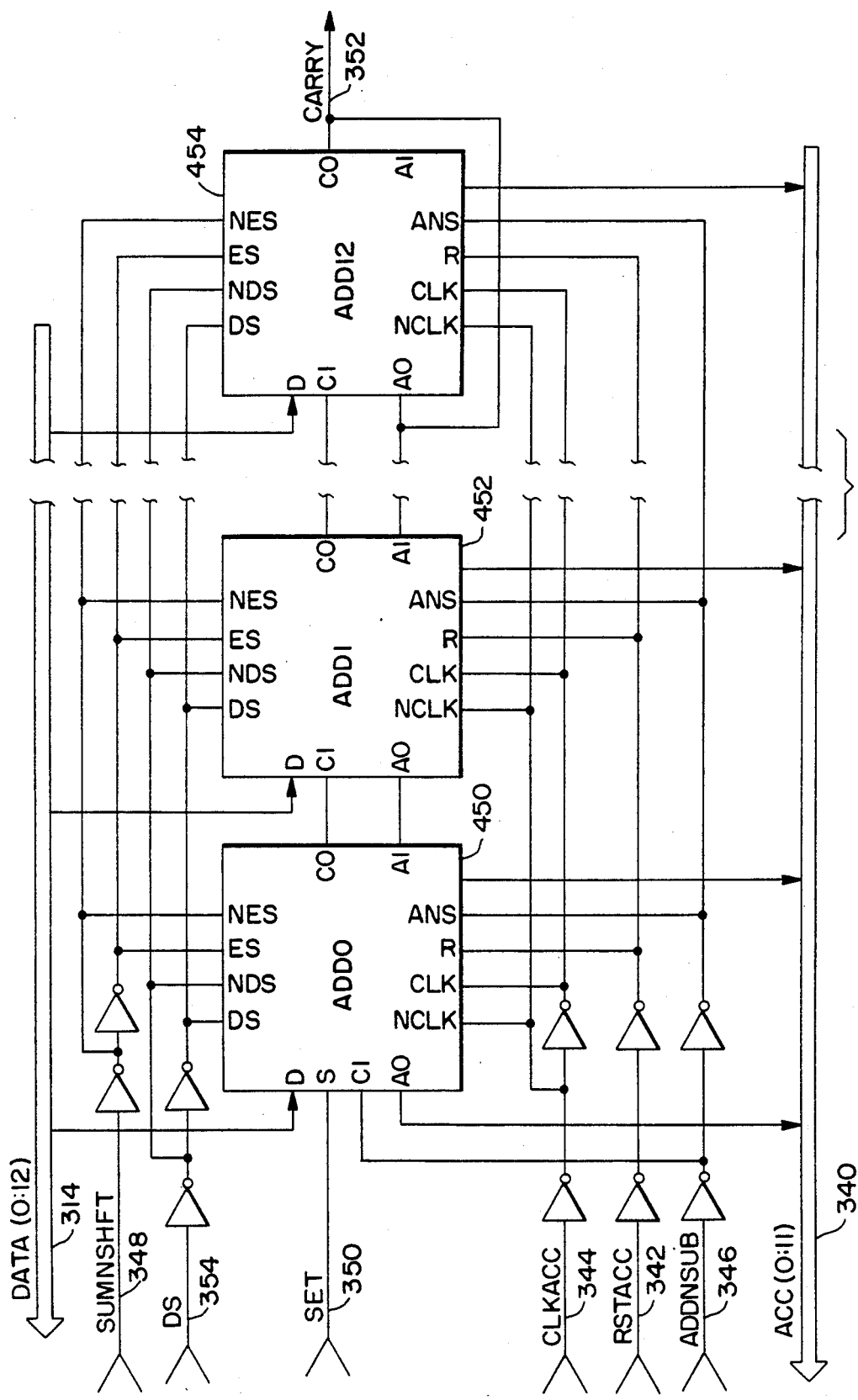
FIG. 8 is a schematic diagram of the arithmatic logic unit functional block illustrated in FIG. 5.

FIG. 8 is a schematic of the ALU 336. The ALU includes 13 full adder cells, cells 1-12 being identical, cell 0 having as an additional feature the ability to have its accumulator output set to 1. Illustrated in FIG. 8 are cell 0 labeled 450, cell 1 labeled 452 and adder cell 12 labeled 454. Adder cells 2-11 are not illustrated but are identical to adder cell 1 and are interconnected with the various inputs and outputs identical to adder cell 1. Each adder cell includes a data input, labeled D, an input and inverted data strobe inputs from DS line 354 (DS, NDS), inputs and inverted inputs of SUMNSHFT line 348 (ES, NES), inputs and inverted inputs from the accumulator clock line CLKACC 344 (CLK, NCLK) an input for the accumulator reset line RSTACC 342(R) and an input from the addition/subtraction selection line ADDNSUB 346 (ANS).

Data stored in each cell is available at the accumulator output AO, the data output of each cell is tied to an accumulator input AI of the next cell, which is used in shifting data from one cell to the next. Each cell includes a carry output CO, which is coupled to the carry input CI, of the next subsequent cell with the exception that the carry output of the accumulator cell 12, labeled 454, is available on the CARRY line 352, provided to the control/sequence logic 330. In response to a positive pulse on set line 350, the accumulator output of adder cell 0, 450, is set to 1. This feature is used when the ALU is used to decrement the pacing rate, as discussed below.

In operation, in the presence of a high signal on DS line 354, the logic level present level at the D input to the cell is passed through to the full adder circuit and is added to the data previously latched into the cell. If a high logic level is present on the ADDNSUB line, the logic level present at the D input to the cell will be passed through to the full adder circuit. If a negative logic level is present on ADDNSUB line 346, the negative of the logic level present at the D input to the cell will be passed through to the full adder circuit. The carry from the addition or subtraction, respectively then appears at the CO carry output of the cell. The result of the addition or the substraction is then latched on the next succeeding clock signal on ACC CLK clock line 344 and is thereafter available at the AO output of the cell.

Addition and subtraction are enabled in response to a high signal level on SUMNSHFT line 348. In the presence of a high signal on this line, the result of the above described subtraction or addition is latched through to the AO output of the cell. If the logic level on SUMNSHFT line 348 is low, a clock signal on the accumulator clock line 344 will cause a shift of the data presently in the cells latching the data present at each AO output of each cell through to the next lower order cell, shifting the total contents of the accumulator one cell to the right. Reset of the accumulator to all zeroes is accomplished by a high signal on the RESETACC line 342.

Figure 9A:
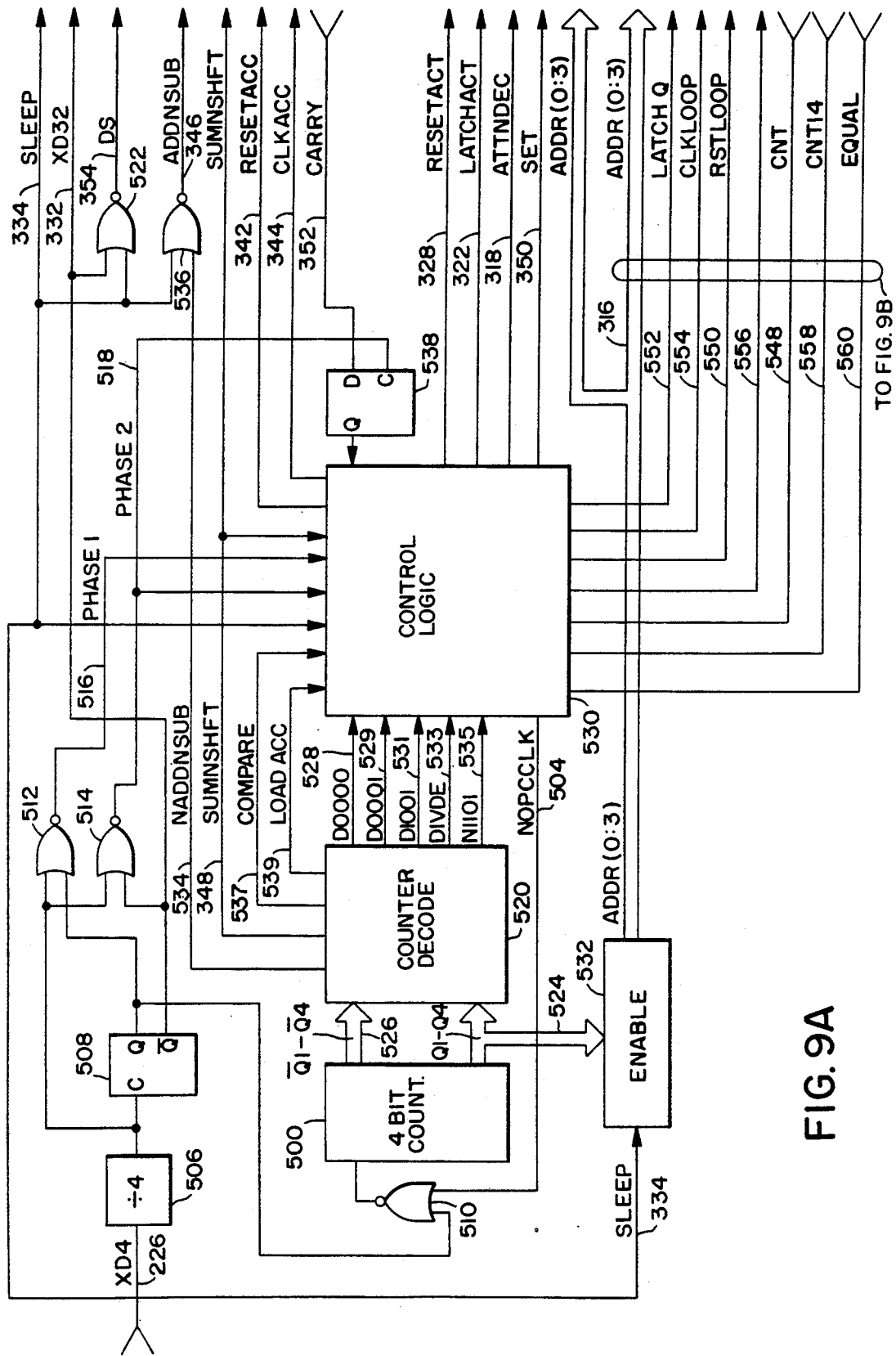
FIGS. 9A and 9B are functional schematic diagrams of the sequence/control logic block illustrated in FIG. 5.
Figure 9B:
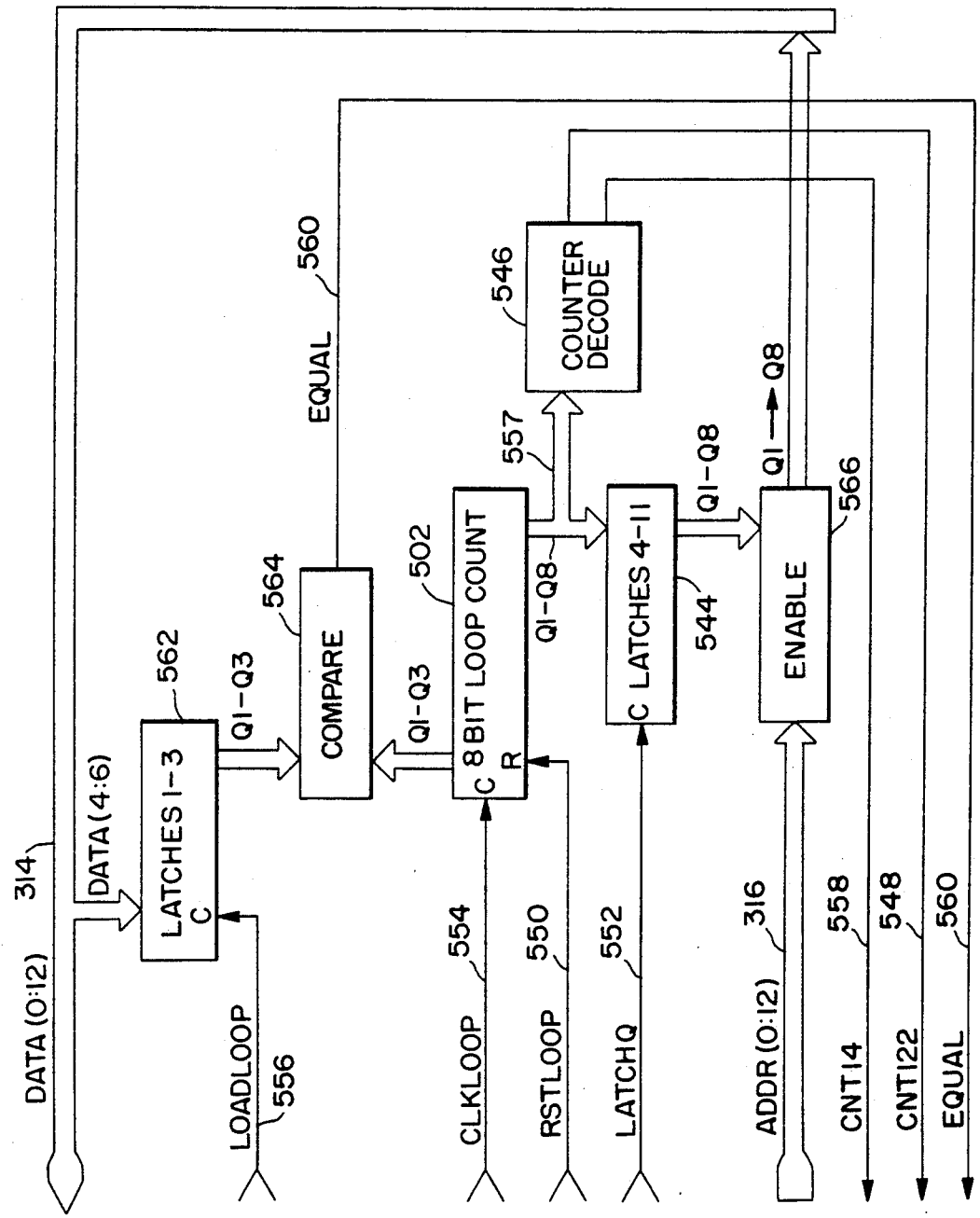

The operation of the accumulator to calculate the pacing rate can best be understood in conjunction with the description of the sequence/control logic illustrated in FIGS. 9A and 9B. FIGS. 9A and 9B should be considered together with the timing diagram illustrated in FIG. 9C and illustrate the sequence/control logic portion of the device. This circuitry controls all functions associated with calculation of the pacemakers escape interval based on the output of the sensor.

Basic operation of the measurement of the sensor output and calculation of the pacing rate falls under the control of a 4 bit counter 500, the outputs of which are used for controlling the operation of the ALU 336, of the program access block 300 and the detect counter 322. 4 bit counter 500, in conjunction with the 8 bit loop counter 502, defines a 250 millisecond cycle. Counter decode logic 520 decodes specific counts and passes them to control logic 520 via lines 528, 529, 531, 533, 535, 537 and 539.

Recalculation of the pacing rate (RRP) occurs once every eight 250 millisecond cycles. This defines the 2 second measurement period used to process the information from sensor processing circuitry 230 discussed above.

Basic timing for the sequence control logic is provided by the 8 KHz clock signals present on XD4 line 226 produced by a divide by 4 from the 32 KHz crystal oscillator. This clock frequency is divided again by four by a two bit counter 506 employed as a divide by four circuit to produce a clock signal divided by 16 from the crystal oscillator. This signal is divided again by two by flip-flop 508 to produce a clock signal divided by 32 from the basic oscillator frequency on XD32 line 332. This clock signal is used by the pacing timing circuitry 338, and provides the basic timing signals used by the sequence/control circuitry illustrated in FIGS. 9A and 9B. The Q output of flip-flop 508, inverted by NOR gate 510 to correspond to the clock signal on XD32 line 332, provides the clock signal for the 4 bit counter 500. This clock signal is enabled in response to a low logic level on NOPCCLK line 504. NOR gates 512 and 514 employ the output of 2 bit counter 506 in conjunction with the Q and not Q outputs of flip-flop 508, respectively, to generate 2 one-quarter duty cycle clock pulses, 180° out of phase with one another during each XD32 clock cycle present on line 232. The signals on PHASE1, line 516 and PHASE2 line 518 provide for several timing signals during each XD32 clock cycle for 4 bit counter 500, allowing sequential steps to be performed during individual XD32 clock cycles. The 1 and 2 clock signals on lines 516 and 518, respectively, are provided to the control logic 530 and, in conjunction with the outputs of counter decode logic 520 are used to control the operation of the activity logic circuitry according to the present invention. Thereafter, these signals shall be referred to as the "phase 1" and "phase 2" clock signals. Clock signal XD32, enabled by NOR gate 522 when SLEEP line 334 is low produces a data strobe signal on DS line 354 which, as discussed above, serves to clock data from the data bus 314 into the ALU 336.

Figure 9C:
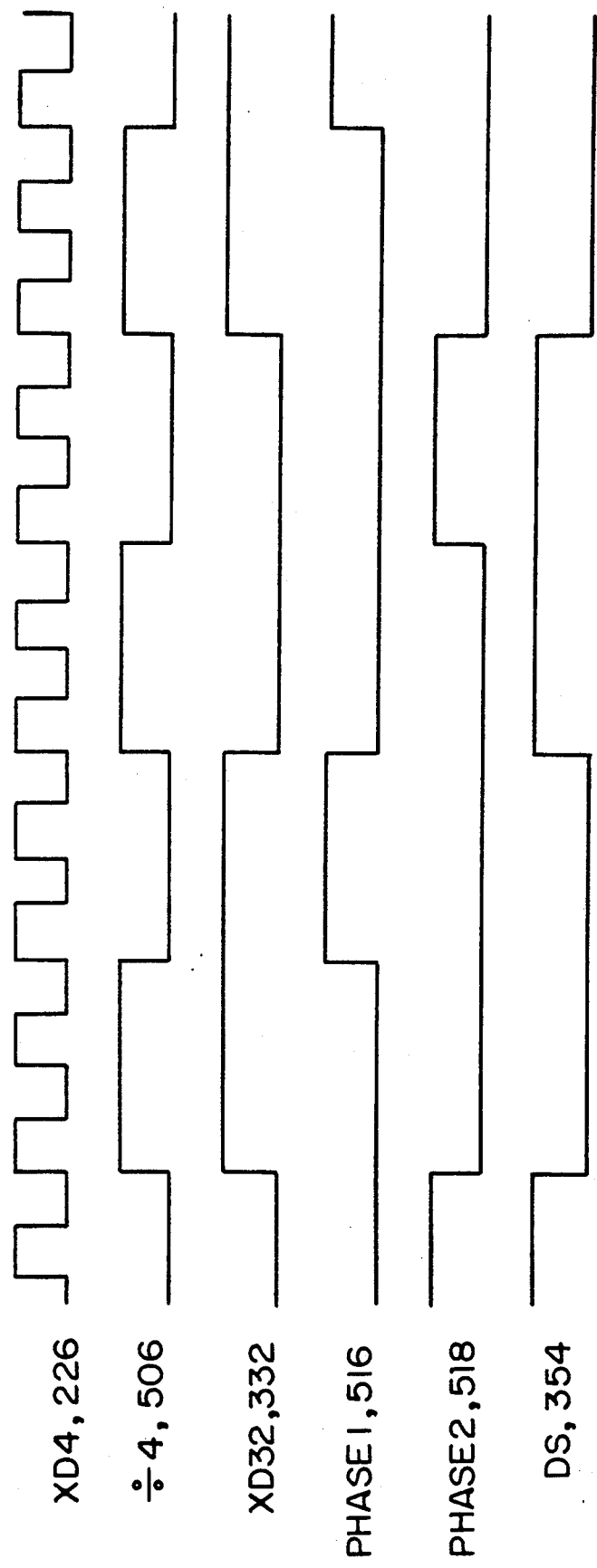
FIG. 9C is a timing chart useful in understanding the operation of the circuitry illustrated in FIGS. 9A and 9B.

Generation of these basic timing signals is illustrated in FIG. 9C. As illustrated, the clock signal on line 332 corresponds to the clock signal applied to the 4-bit counter 500. The clock signals on PHASE1 line 516 and PHASE2 line 518 provide timing references ¼, ½, and ¾ of the way through the XD32 clock cycle. The data strobe signal on DS line 354 begins at the midpoint of the XD32 clock cycle.

Counter decode logic 520 provides control signals to control logic 530. D0000 line 528, D0001 line 529, N1101 line 535 and D1001 line 531 are set high during their indicated counts decoded from counter 500. Divide line 533 is set high during count 0101, LOADACC line 539 is high during counts 0001, 0100, 0110, 1001 and 1111, enabling reset of the ALU 336 via RESETACC line 342. Compare line 537 is set high during count 1000, and disables the accumulator clock on CLKACC line 344.

Operation of the sequence/control logic is best understood by following the operation of the logic through a 250 millisecond cycle in which calculation does not occur, and then following the operation of the circuitry during the 250 millisecond cycle in which recalculation of the pacing rate occurs.

The 250 ms cycle is initiated by rollover of the 4 bit counter 500 to a count of 0000. Q outputs of the counter are present on 4 bit bus 524. Not Q outputs are present on line 526. In response to a count of all 0's, control logic 530 sets SLEEP line 334 low with the PHASE1 clock signal, allowing enabling circuitry 532 to pass the Q1-Q4 outputs of counter 500 through to the 4 bit ADDR bus 316. Concurrently, the clock signal on PHASE2 line 518 is passed through to the accumulator clock line 344. SLEEP line 334 going low also enables the inverse of the clock signal on XD32 line 332 to be passed through NOR gate 522 to form at the data strobe signal on DS line 354. As discussed above, the presence of the code 0000 on the ADDR bus triggers select logic 420 (FIG. 7A) to apply a 1 to line 9 of DATA bus 314 and thereby to the D input of cell 9 of the arithmatic logic unit 336 (FIG. 8).

During a count of 0000, counter decode circuitry 520 places a low logic level signal on NADDNSUB line 534 which is inverted by NOR gate 536 to provide a high signal on 80 ADDNSUB line 346. SUMNSHFT line 348 is set high so that on the leading edge of the phase 2 clock signal on line 518 the ALU will be clocked, adding a count of one to cell 9 of the ALU.

During the 250 millisecond cycles in which calculation does not occur, the 4 high order cells, 9, 10, 11 and 12 of the ALU act as a 4-bit counter. They are preset to a count of 8 by resetting the ALU and adding a 1 to cell 12. Each time the 4-bit counter 500 rolls over, the ALU is incremented by a count of 1 at cell 9. After 8 250 millisecond cycles, the 4-bit counter comprised of cells 9–12 of the ALU 336 rolls over and the carry output on line 352 goes high. As discussed below, this triggers the calculation cycle. When 4-bit counter 500 rolls over to 0000, the value on CARRY line 352 is latched into flip-flop 538 by the phase 2 clock signal on line 518. This serves to save the carry output so that it may be used by the control logic 530. Assuming that CARRY line 352 is not set (logic 0) on the count of 0001 by 4-bit counter 500, control logic 530 sets SLEEP line 334 high preventing the Q outputs of counter 500 from passing through to ADDR bus 316.

Counter 500 continues to count to a count of 0101 setting DIVIDE line 533 high, triggering the generation of a pulse concurrent with the phase 1 clock signal on line 516, which resets the loop counter 502 via RSTLOOP line 550. On the trailing edge of the same phase 1 clock cycle, NOPCCLK line 504 is set high disabling NOR gate 510 from passing clock signals through to bit counter 500. On the next subsequent phase 1 clock signal, a positive loop counter latch signal is generated on LATCHQ line 552 which latches the outputs of the loop counter 502 through to latches 544 via 8 bit data bus 557 which also provides the output of the loop counter to the counter logic 546. On the next subsequent phase 2 clock signal, loop counter clock signals which are inverted phase 2 clock signals, are applied to CLKLOOP line 554. Counter decode logic 546 detects a count of 224 at which point a high signal is placed on CNT 224 line 548. This signal is applied to control logic 530, and on the leading edge of the next succeeding phase 2 clock signal, a low logic signal is placed on NOPCCLK line 504 enabling 4 bit counter 500 to resume counting on the subsequent XD32 clock cycle. Counter 500 continues to count until it reaches a count of 1011. On reaching this count, counter decode logic 520 sets SUMNSHFT line 348 low. In response, control logic 530 generates a reset pulse on RSTLOOP line 550 resetting loop counter 502 concurrent with the next phase 1 clock signal and sets NOPCCLK line 504 high on the trailing edge of the same phase 1 clock signal, again disabling bit counter 500. Concurrent with the next subsequent phase 2 clock signal, a pulse is generated on LOADLOOP line 556. On the next subsequent phase 2 clock cycle on line 518, clock signals resume on CLKLOOP line 544, clocking loop counter 502 until counter logic 546 decodes a count of 14 setting CNT14 line 558 high.

In response to a high signal on CNT14 line 558, control logic 530 sets NOPCCLK line low at the leading edge of the next succeeding phase 2 clock signal, enabling clocking of 4 bit counter 500. 4 bit counter 500 continues to count until it rolls over to a count of 0000 at which point the 250 millisecond cycle resumes again.

Assuming that the final 4 stages of the ALU, cells 9–12, contain a count of 1111, on the next count of 0000 by counter 500, a calculation cycle begins. As described above, in response to a count of 0000 by counter 500, counter decode circuitry 520 triggers control logic 530 to set the SLEEP line 334 low enabling passage of the 0000 count through to ADDR bus 316 where it in turn triggers select logic 420 to place a logic 1 on the ninth line of the DATA bus 314. Control logic 530 on the next subsequent phase 2 clock signal generates a clock signal on CLKACC line 344 which allows the ALU to overflow, setting CARRY line 352 high. The high level on CARRY line 352 is clocked through to the control logic 530 on the rising edge of the next phase 2 clock signal, allowing SLEEP line 344 to remain low so that the Q outputs of the 4 bit counter 500 continue to be available on ADDR bus 316.

At a count of 0001, control logic 530 supplies a positive pulse concurrent with the phase 1 clock cycle to the LATCH ACT line 322, latching the logic levels on the Q outputs of the 5 bit detect counter 400 (FIG. 6) into one of latches 402 and 404. On the next subsequent phase 2 clock signal, control logic 530 generates a reset pulse on RESATACT line 328 which resets 5 bit counter 400. As described above, latches 402 and 404 between them now carry the cumulative detect counts over the preceeding 4 second interval.

During count 0001, select logic 420 places the value present on DTERM bus 302 on to lines 0–7 of DATA bus 314 and RSTAE line 342 is pulsed high to clear the ALU. ADDNSUB line 346 is set high as is SUMNSHFT line 348. On the trailing edge of the next phase 1 clock signal, DS line 354 goes high, loading the logic levels on data bus 314 into the ALU. During the next subsequent phase 2 pulse, a clock signal is generated on CLKACC line 344 which adds the values on the DATA bus 314 to the ALU 336. The ALU now holds the programmed value for the D-term used to calculate pacing rate.

On a count of 0010 on ADDR bus 316, select logic 414 associated with detect counter 400 is activated, supplying the Q outputs of latches 400 to lines 0:4 of data bus 314. On the trailing edge of the next successive phase 1 clock signal, this data is loaded into the ALU and on the next subsequent phase 2 signal, it is added to the value of the D-term previously stored in the ALU.

On a count of 0011 by 4 bit counter 500, select logic 414 supplies the contents of latches 404 to lines 0:4 of DATA bus 314. On the trailing edge of the next successive phase 1 clock signal, this data is loaded into the ALU and during the next subsequent phase 2 clock signal, it is added to the number present in the ALU. The ALU 336 now contains the sum of the programmed D term along with the total number of activity detects over the preceding four second interval. This value is latched into a 12 bit (FIG. 10) division register 600 located in the timing logic circuitry 338 in response to the NLDDVSR line 616 going low concurrent with the &.railing edge of the data strobe pulse on DS line 354.

During count 0100 by 4 bit counter 500, the ALU is reset by control logic 530 concurrent with the leading edge of the phase 1 clock signal by means of a reset pulse on RSTACC line 342. In response to a count of 0100, select logic 420 applies the information present on the BTERM bus 202 to lines 0–12 of the DATA bus 314. This value is loaded into the ALU on the leading edge of the DS signal on line 354 and added to the accumulator by the accumulator clock signal on CLKACC line 344 concurrent with the phase 2 clock signal.

During a count of 0101 by counter 500, DIVIDE line 542 is set high, and ADDNSUB line 346 is set low so that the ALU will subtract rather than add. On the trailing edge of the phase 1 clock signal, NOPCCLK line 504 is set high disabling further counting by 4 bit counter 500. Concurrent with the phase 1 clock signal, a reset pulse is generated on RSTLOOP line 550 which resets loop counter 502 (FIG. 9B). On the trailing edge of the same phase 1 clock signal, the clock to the ALU on CLKACC line 344 is disabled by the control logic 530, and on the next subsequent phase 2 clock signal, clocking of the loop counter 502 by means of a signal corresponding to the negative of the phase 2 clock signal on CLKLOOP line 518 begins.

Figure 10:
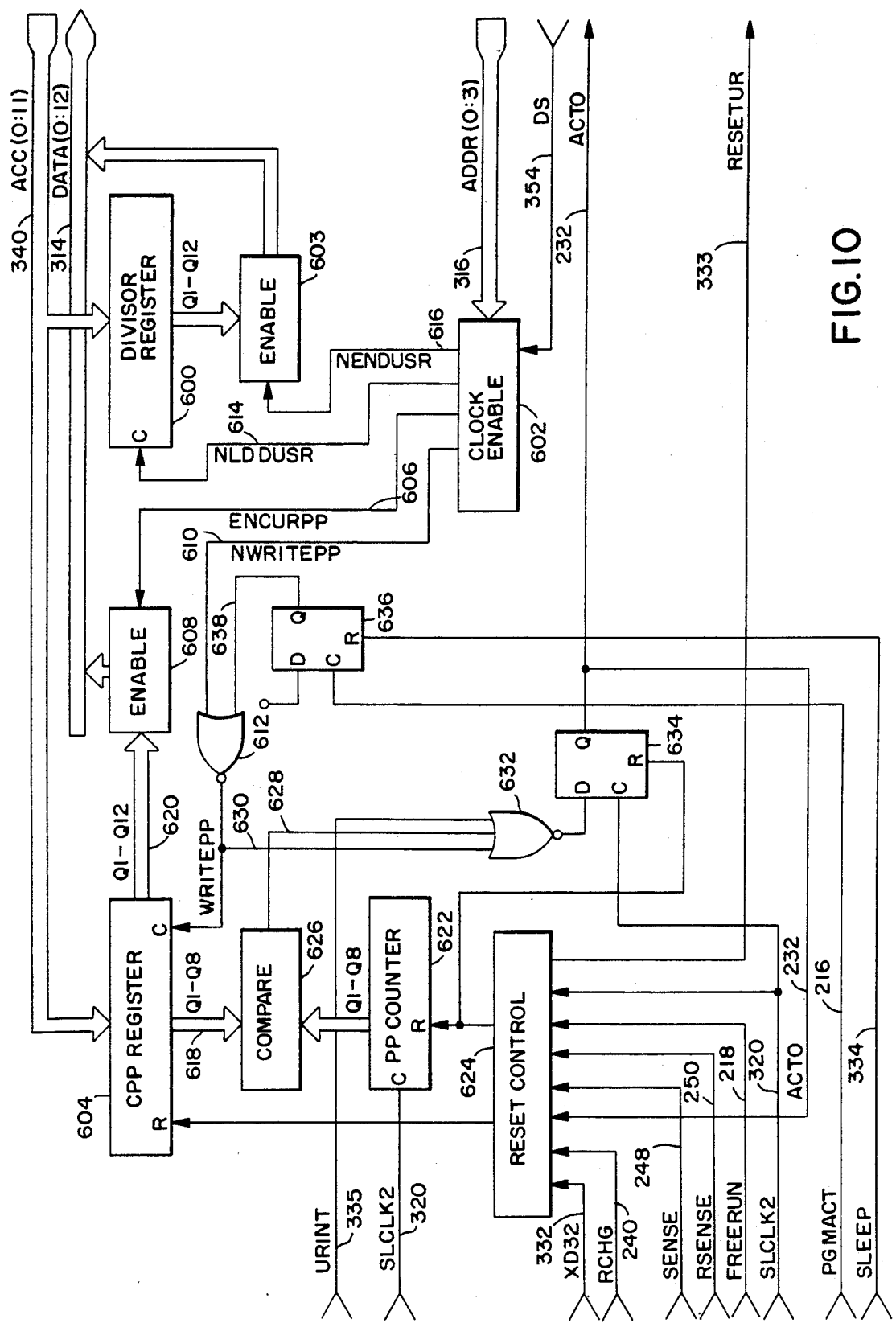
FIG. 10 is a functional schematic diagram of the pacing logic illustrated in FIG. 5.

In response to the 4 bit counter 500 reaching the count of 0101, clock enable circuitry 602 in the timing logic illustrated in FIG. 10 goes low, placing the divisor stored in the divisor register 600 (FIG. 10) on lines 0-11 of DATA bus FIG. 314. Concurrent with the leading edge of the next phase 2 clock signal, the ALU 336 is clocked by means of a clock pulse on CLKACC line 344, subtracting the divisor contained in register 600 from the B-term loaded into the ALU. On the next subsequent phase 2 clock signal, the loop counter 502 is clocked by means of an inverted version of the phase 2 clock signal on CLKLOOP line 554.

As during the 250 ms cycles which did not involve recalculation of the pacing interval, the loop counter continues to count until it reaches a count of 224. For each clock cycle of the loop counter, the divisor is substracted from the B-valve in the ALU 336 until CARRY line 352 goes low, indicating the end of the division process. In response to line 352 going low, control circuitry 530 generates a latch pulse on LATCH Q line 552, which latches the then current count of the loop counter 502 into latches 544. This number is later used to calculate the pacing interval. However, the loop counter 502 continues to count until it reaches a count of 224, generating a high signal on CNT 224 line 548. In response to the count of 224 being achieved, the control logic 530 sets NOPCCLK line 504 low on the leading edge of the next succeeding phase 2 clock signal, enabling clocking of four bit counter 500.

In response to a count of 0110 by counter 500, control logic 530 generates a reset signal concurrent with the phase 1 clock signal on the RSTACC line 342 which resets the ALU 336. In response to a count of 0110, enable logic 560, asociated with loop counter 502 places the division count contained in latches 544 on lines 4-11 of DATA bus 314. This value is loaded into the ALU on the next rising edge of the DS pulse on line 354, and is latched into the accumulator during the next subsequent phase 2 clock signal, by means of an accumulator clock pulse on CLKACC line 344. The division result is loaded into cells 4-11 of the accumulator.

In response to a count of 0111, select logic 420 places the information on ATERM bus 201 on lines 4-12 of the databus. This value is loaded into the ALU on the leading edge of the DS pulse on line 354 and added to the value of the present in the ALU by means of a clock pulse on CLKACC line 344. The resultant sum represents the initial calculation of the desired pacing interval (RRP).

In response to a count of 1000, select logic 420 places the information present on UR bus 204 on lines 4-10 of DATA bus 314 and counter decode logic 520 sets ADDNSUB line 346 low, indicating that the ALU is to subtract. The upper rate value is loaded into the ALU on the rising edge of the next subsequent data strobe pulse on DS line 354, generating a negative logic level on CARRY line 352 if the upper rate value is greater than the value present in the ALU and a positive logic signal on CARRY line 352 if the upper rate value is less than the value in the ALU.

During a count of 1001 by counter 500, if CARRY line 352 was set low, as latched into flip-flop 538, a reset pulse is generated on RSTACC line 342 concurrent with the phase 1 clock signal, followed by clocking the upper rate value into the ALU with the leading edge of the next phase 2 clock signal using a clock pulse on line 344. This insures that the desired pacing rate calculated by the accumulator is always less than or equal to the programmed upper rate, regardless of the output of the activity sensor. If CARRY line 352 was set high, the calculated RRP remains in the ALU.

During count 1010 of counter 500, ADDNSUB line 346 is set low, and the value of the current pacing interval stored in register 604 in the pacing timing logic 338 (FIG. 10) is placed on lines 0-11 of the DATA bus 314 by clock enable circuitry 602 which enables application of the Q outputs of the current pacing period register 604 (FIG. 10) to DATA bus 314 by means of a high signal on ENCURPT line 606. This passes the Q outputs of register 604 through to DATA bus 314 via enable logic 608. The data indicative of the current pacing period is loaded into the ALU on the rising edge of the next subsequent DS pulse on line 354, and is subtracted from the value stored in the ALU, which corresponds to the desired pacing rate (RRP) on the rising edge of the next subsequent phase 2 clock signal. If the subtraction result is negative, indicating that the desired rate is greater than the present rate (desired escape interval is less than the present escape interval), the CARRY line 352 will be low, indicating that a rate increase is required. If CARRY line 352 is high, indicating that the present pacing rate is greater than the desired pacing rate, a rate decrease is specified.

In response to a count of 1011, and a high signal on ATTNDEC line 320, the programmed acceleration or attack value, present on ATBUS 206 is placed on lines 0-2 of the data bus 314. In response to a count of 1011 and a low signal on ATTNDEC line, the value of the decay or decelleration setting present on DEC bus 205 is placed on lines 0-2 of the data bus. This information is loaded into latches 562 in response to a positive signal on load loop line 556. During count 1011 of counter 500, counter decode logic 520 sets SUMNSHFT line 348 low, enabling the accumulator to shift, rather than add. During the phase 1 clock signal on line 516, a reset signal is generated on RSTLOOP line 550, resetting loop counter 502 followed by generation of a set pulse on LOADLOOP line 556 which loads the value on the DATA bus 314 into latches 562.

ATTNDEC LINE 320 is set high if the carry bit resulting from the subtraction of the present pacing interval from the desired pacing interval was low, and is set low if the carry value resulting from the subtraction was high. Both the attack and decay parameters correspond to the number of right shifts performed by the ALU on the value indicative of the difference between desired pacing interval (RRP) and the current pacing interval, stored therein. Shifting of the ALU occurs in a manner analogous to the previous repeated divisions performed by the accumulator, and is monitored by the loop counter 502. Also during count 1011, concurrent with the leading edge of the phase 2 clock signal, NOPCCLK line 504 is set high disabling counter 500. As in the previous 250 ms measurement cycle in which calculation was not performed, the loop counter is clocked until a count of 14 is reached. For each clocking of the loop counter, a clock signal is generated on CLKACC line 344 which shifts the value stored in the ALU one cell to the right. When the number of shifts as counted by loop counter 502 equals the number of shifts determined by the acceleration or deceleration parameter stored in latches 562 (FIG. 9B), their equivalence is detected by compare logic 564 which generates a high logic signal on EQUAL line 560. This is provided to the control logic circuitry 530, and disables further clocking of the ALU. The value now stored in the ALU represents the incremental change to the present pacing rate interval, positive or negative.

It is important to note that if the pacing rate is being decremented (pacing interval increased), set line 350 is held high ensuring that at least a minor decrement is obtained, even if the value in the ALU would otherwise be all zeros after shifting. This feature assures a return to the base rate on cessation of exercise.

Loop counter 502 continues to count until it reaches a count of 14, triggering counter logic 546 to place a high logic signal on CNT 14 line 558, which triggers control logic 530 to set NOPCCLK line 504 low on the leading edge of the next succeeding phase 2 clock cycle, reenabling the Q outputs of counter 500 to pass through to ADDR bus 316. Clock enable circuitry 602 (FIG. 10) places the contents of the pulse period register 604 on lines 0-11 of the DATA bus 314, which are loaded into the ALU on the next subsequent DS pulse on line 354. The stored increment or decrement in the ALU is added to value of the current pacing period concurrent with the next phase 2 clock signal. This arrangement provides a pacemaker which asymptotically approaches the desired pacing interval (RRP) for any particular level of physical output. This also prevents excessively rapid changes in pacing rate.

During the count of 1101 by counter 500, clock enable logic 602 in pacing timing circuitry 348 (FIG. 10), by means of a low signal on NWORITEPP line 610 and NORGATE 612, latches the contents of the ALU, present on ALU bus 340 into the current pulse period register 604. The number loaded in register 604 is the number of slow clock pulses corresponding to the escape interval of the pacemaker, previously referred to as "RRP".

Counter 500 continues to count until it reaches a count of 1111. In response to a count of 1111 on the ADDR bus 316, select logic 420 (FIG. 7A) places a value of 1 on line 12 of the data bus 314, holding all other lines of the data bus low. As noted above, the four highest order cells of the ALU are used as a 4 bit counter when calculations are not taking place, keeping track of the number of 250 ms cycles. On the leading edge of the data strobe pulse on DS line 354, the value 1 is loaded into the cell 12 of the ALU, and on the leading edge of the next phase 2 clock signal is latched into the ALU. This corresponds to an initial count of 8, as discussed above. During the 250 ms cycles in which calculation does not take place, a value of 1 is added to cell 9 of the ALU for each 250 ms cycle. With the initial count of 8, the ALU will thus overflow after eight 250 ms cycles, setting the CARRY line 352 high and beginning another measurement cycle.

As counter 500 rolls over, placing a value of 0000 on the address bus 316, the next 250 ms cycle is begun, as described above.

FIG. 10 illustrates the timing logic 338 which determines the escape interval of the pacemaker. It also includes a divisor storage register 600 for storing the value of the programmed D-term added to the number of detects counted by the detect counter during the previous four seconds. As discussed above, this value is used in calculating the escape interval of the pacemaker (RRP) according to the equation $RRP = A + (B/(4(s) + D))$, with the number of detects counted during the previous four seconds corresponding to 4(s), where "s" represents the frequency of detects per second counted by the detect counter 332.

The current pacing period is stored in 12-bit register 604. The Q outputs of the highest 8 stages of the register 604 are available on bus 618, and the Q outputs of all 12 stages of the register are available on 12-bit bus 620. The Q outputs of register 604 are placed on data bus 314 in response to a high signal on ENCURPP line 606, generated by clock enable circuitry 602 in response to a count of 1010 or 1100 on ADDR bus 316, passing the Q outputs through enable circuit 608 to DATA bus 314.

The basic timing of the escape interval is accomplished by pacing period counter 622, which is reset by reset control 624 in response to a high signal on RCHG line 240 or on sense line 248. Normally, the clock signal present on XD32 line 332 is used to clock through the asynchronously occurring signals on sense line 248, so that their timing corresponds to the timing in the remainder of the circuit.

The clock signal present on 2 line 320 provides the clock signal for counter 622. Upon reaching a count corresponding to that in register 604, compare circuitry 626 generates a high signal on line 628. Assuming that the upper rate interval has expired, indicated by a low logic level on URINT line 343 and that register 604 is not being written to, indicated by a low signal on line 630, the low signal generated by compare logic 626 will pass through NORGATE 632, and will be clocked through flip-flop 634 on the next slow clock cycle on 2 line 320 to generate a positive logic level on ACTO line 232, which will trigger generation of a pacing pulse by the output amplifier 236.

When FREERUN line 218 is high, reset control logic 624 provides a reset to counter 622 only in response to a high signal on ACTO line 232. In this mode, the pulse generator generates output pulses asynchronously at the pacing rate corresponding to the data in register 604. Reset control logic 624 also generates a reset signal for the upper rate counter 424 (FIG. 7B) on RESETUR line 333. A reset pulse is generated on this line in response to a positive logic level on any of RCHG line 240, sense line 248, or R sense line 250. If free run line 218 is high, a high logic level on RESETUR line 333 is generated only in response to a high logic level on ACTO line 232.

PGMACT line 216, from the program logic 210, is at a high logic level during reprogramming of parameters related to the calculation of the activity based escape interval. When this signal goes high, it clocks flip-flop 636, which generates a high logic level on lines 638, preventing writing to register 604 and updating of the pacing rate. Flip-flop 636 is reset by SLEEP line 334 going high, reenabling writing to register 604. As discussed above, after calculation of a new escape interval (RRP) by the ALU 336, present on ALU bus 340, clock enable circuitry 602 generates a low logic signal on NWRITPP line 610 in response to a count of 1101, loading the new value for the escape interval (RRP) into register 604.

The above described pacemaker is disclosed as implemented with full custom digital logic circuitry. However, it is also believed readily implemented in the form of a microprocessor based pacemaker as well. Further, although calculation of the desired parameters (A-term, B-term, D-term) for accomplishing the desired relationship between physical activity and pacing rate is accomplished by means of a programmer which provides the desired values by reference to a look up table, it is also believed within the scope of the invention to generate the desired variables by means of a mathematical calculation by the programmer, or internally within the cardiac pacemaker, particularly in microprocessor based versions of the device.

Although the specification discloses a single chamber pacemaker which would operate in the VVIR or AAIR mode, the invention is also equally applicable to dual chamber pacemakers of all types, including DDDR, DDIR, VDDR and DVIR type pacemakers. In such embodiments, the interval to be varied with activity may conveniently be the interval between atrial pacing pulses (DVIR and DDR), the interval between ventricular pacing pulses (DDDR, DDDIR, VDDR and DVIR) or the interval between a ventricular pulse and the next subsequent atrial pacing pulse (DDDR, DDIR, and DVIR). Moreover, the present invention is also believed to be useful in the context of multiple sensor pacemakers, in which the pacing rate is determined by a plurality of measured physical parameters. In such embodiments, the desired pacing interval (RRP) for one sensor might be combined with the desired pacing interval (RRP) for another sensor by weighted or unweighted averaging or by other methods.

Although the specification discloses a device in which the specified rates selected by means of the programmer are the upper and lower rates, the invention also allows for selection of other predetermined relationships between pacing rate and sensor output. For example, as the equation set forth includes three variables, it is also capable of defining non-linear rate response, primarily through alteration of the A-term. For example, the physician might select the lower rate, the upper rate and an interim rate by means of the programmer, which would employ a lookup table to generate corresponding A, B and D terms. For example, the function defined by the equation might increase from the lower rate at no activity, up through a predetermined interim rate at a first predetermined sensor output, and then through to a predetermined upper rate at a second preselected sensor output. The basic invention provides for substantial flexibility in defining the function relating to pacing rate to sensor output and, with appropriate lookup tables stored in the external programmer, can provide for customized rate response curves as desired by the physician.

As such, the above specification should be considered exemplary, rather than limiting, with regard to the following claims

We claim:

1. In a cardiac pacemaker comprising a pulse generator for generating stimulus pulses, sensor means for sensing physiologic demand for oxygenated blood and for generating a sensor output variable between first and second levels and sensor processing circuitry for processing said sensor output and for controlling the rate of stimulus pulses generated by said pulse generator as a function of said sensor output, the improvement wherein:

said sensor processing means comprises means for independently selecting a first rate, a second rate and one of a plurality of predetermined sensor output levels between said first and second levels and means for defining a function relating the rate of stimulus pulses generated by said pulse generator to the output from said sensor, said stimulus pulse rate determined by said function increasing from said first rate when said sensor output is at said first level to said second rate when said sensor output is at said selected one of said plurality of predetermined sensor output levels.

2. A cardiac pacemaker according to claim 1 wherein said function is a monotonic function relating said stimulus pulse rate to the output of said sensor.

3. A pacemaker according to claim 2 wherein said function is a linear function relating said stimulus pulse rate to the output of said sensor between said first level and said selected one of said plurality of predetermined sensor output levels.

4. A pacemaker according to claim 1 or claim 2 or claim 3 wherein said means for selecting said first rate, second rate and said selected one of said predetermined sensor output levels comprises an external pacemaker programmer and wherein said means for defining said function is located within an implantable cardiac pacemaker, said function selected in response to selection of said first rate, second rate and selected sensor output level.

5. A pacemaker according to claim 4 wherein said function takes the form:
RRP=MAXIMUM(A+(B/(sensor output+D))UR), wherein RRP represents the interval between successive stimulus pulses generated by said pulse generator UR is the time interval corresponding to the maximum pacing rate, and A, B and D are terms generated in said external programmer as a function of the selection of said first rate, second rate and selected sensor output level.

6. A cardiac pacemaker comprising:

a pulse generator for generating stimulus pulses, a sensor for sensing physiologic demand for oxygenated blood, of the type which generates sensor output signals at an increasing frequency as the demand for oxygenated blood increases, said frequencies ranging between a first frequency and a second frequency; and sensor processing means for processing said output of said sensor and for controlling the rate of stimulus pulses generated by said pulse generator as a function of the frequency of said output from said sensor;

wherein said sensor processing means comprises means for independently selecting a lower rate, an upper rate, and one of a plurality of predetermined sensor output frequencies between said first frequency and said second frequency, and means for defining a function relating the rate of generation of said stimulus pulses by said pulse generator to the frequency of said output of said sensor, said function increasing said pacing rate from said lower rate when said output of said sensor is at said first frequency to said upper rate when said output of said sensor is at said selected one of said plurality of predetermined frequencies.

7. A pacemaker according to claim 6 wherein said function takes the form RRP=MAXIMUM (A+(B/(sensor frequency+D))UR), wherein RRP signifies the interval between stimulus pulses generated by said pulse generator, UR signifies the interval corresponding to the upper rate and A, B and D are terms selected as a function of said upper rate, lower rate and selected one of said predetermined frequencies.

8. A cardiac pacemaker according to claim 1 or claim 6 wherein said sensor processing means further comprises means for limiting the rate of change of the rate of generation of said stimulus pulses in response to changes in the output from said sensor.

9. A cardiac pacemaker according to claim 1 or claim 6 wherein said sensor is responsive to detected physical activity.

10. A pacemaker as claimed in claim 1 or claim 6 above wherein said sensor processing means is responsive to the selection of a new second rate and in response thereto defines a new function such that said newly selected second rate is accomplished on said sensor output reaching said selected sensor output level.

11. A cardiac pacemaker system comprising:
a pacing pulse generator;
a sensor responsive to physiologic demand for oxygenated blood and which generates a sensor output in response thereto variable between at least first and second levels;
a programmer which allows independent selection of a first rate, a second rate, and a pre-determined sensor output level among a plurality of pre-determined rates and sensor output levels and which provides signals indicative of the selected first rate, second rate and pre-determined sensor output; and
rate control circuitry responsive to said signals from said programmer for defining a function relating the rate of pacing pulses generated by said pulse generator to the output from said sensor, said pacing pulse rate determined by said function increasing from said selected first rate when said sensor output is at said first level to said selected second rate when said sensor output is at said selected one of said plurality of pre-determined sensor output levels, said rate control circuitry responsive to the selection of a new value for said second rate to define a new function such that said newly selected second rate is accomplished on said sensor output reaching said previosly selected sensor output level.

12. A pacemaker system according to claim 11 wherein said sensor is responsive to detected physical activity.

13. A pacemaker system according to claim 12 wherein said sensor output varies at least between first and second frequencies, said first frequency corresponding to said first output level, said second frequency corresponding to said second output level.

14. A pacemaker system according to claim 11 wherein said function takes the form:
RRP=MAXIMUM (A+(B/(sensor output+D)),UR), wherein RRP represents the interval between successive pacing pulses generated by said pulse generator, UR is the time interval between successive pacing pulses generated by said pulse generator at said second selected rate, and A, B, and D are terms generated in said programmer in response to the selection of said first rate, said second rate, and said selected sensor output level.

* * * * *